US011259930B2

(12) United States Patent
Vogt

(10) Patent No.: US 11,259,930 B2
(45) Date of Patent: Mar. 1, 2022

(54) PARTICULATE ALLOPLASTIC BONE REPLACEMENT MATERIAL, AND METHOD FOR PRODUCING A FREE-FORMED POROUS BODY

(71) Applicant: HERAEUS MEDICAL GMBH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 261 days.

(21) Appl. No.: 16/039,043

(22) Filed: Jul. 18, 2018

(65) Prior Publication Data

US 2018/0318087 A1    Nov. 8, 2018

Related U.S. Application Data

(63) Continuation of application No. 15/144,143, filed on May 2, 2016, now abandoned.

(30) Foreign Application Priority Data

May 13, 2015    (DE) .................... 10 2015 107 600.4

(51) Int. Cl.
*A61F 2/28*        (2006.01)
*A61L 27/04*      (2006.01)
(Continued)

(52) U.S. Cl.
CPC ................ *A61F 2/28* (2013.01); *A61L 27/04* (2013.01); *A61L 27/14* (2013.01); *A61L 27/28* (2013.01);
(Continued)

(58) Field of Classification Search
CPC .............. A61F 2/28; A61F 2002/30467; A61F 2002/3092; A61F 2230/0093;
(Continued)

(56) References Cited

U.S. PATENT DOCUMENTS 2,717,437 A    9/1955    De Mestral
3,408,705 A    11/1968    Kayser et al.
(Continued)

FOREIGN PATENT DOCUMENTS

CH        295638 A      1/1954
DE        1625396 A1    6/1970
(Continued)

OTHER PUBLICATIONS

English Translation of German Office Action for related German Patent Application No. 10 2015 107 600.4 dated Jul. 14, 2015.
(Continued)

*Primary Examiner* — Christopher D. Prone
(74) *Attorney, Agent, or Firm* — Norris McLaughlin, P.A.

(57) ABSTRACT

Particulate alloplastic bone replacement material and methods have a multitude of particles, wherein the particles have a core and at least six pins extending from the core, wherein the pins each have at least one connecting element, and wherein the pins are deformable elastically such that, upon multiple particles being pressed together, the connecting elements of different particles interlock with and/or snap into each other and the particles that are interlocked with and/or snapped into each other form an open-pored body of particles that are interlocked with and/or snapped into each other.

23 Claims, 14 Drawing Sheets

(51) Int. Cl.
*A61L 27/14* (2006.01)
*A61L 27/28* (2006.01)
*A61L 27/54* (2006.01)
*A61L 27/56* (2006.01)
*A61F 2/30* (2006.01)

(52) U.S. Cl.
CPC ........... *A61L 27/54* (2013.01); *A61L 27/56* (2013.01); *A61F 2002/30062* (2013.01); *A61F 2002/3092* (2013.01); *A61F 2002/30303* (2013.01); *A61F 2002/30467* (2013.01); *A61F 2002/30985* (2013.01); *A61F 2230/0041* (2013.01); *A61F 2230/0093* (2013.01); *A61F 2310/00017* (2013.01); *A61F 2310/00023* (2013.01); *A61F 2310/00131* (2013.01); *A61L 2430/02* (2013.01)

(58) Field of Classification Search
CPC ....... A61F 2002/30303; A61L 2430/02; A61L 27/40; A61L 27/56
See application file for complete search history.

(56) References Cited

U.S. PATENT DOCUMENTS

| | | | |
|---|---|---|---|
| 4,290,174 A | 9/1981 | Kalleberg | |
| 5,077,870 A | 1/1992 | Melbye et al. | |
| 5,676,700 A * | 10/1997 | Black | A61F 2/28 623/23.28 |
| 5,755,797 A | 5/1998 | Baumgartner | |
| 6,149,689 A * | 11/2000 | Grundei | A61F 2/30767 623/23.5 |
| 2005/0027366 A1 | 2/2005 | Saini et al. | |
| 2008/0244878 A1 | 10/2008 | Hoehe et al. | |
| 2010/0001152 A1 | 1/2010 | Golle et al. | |

FOREIGN PATENT DOCUMENTS

| | | |
|---|---|---|
| DE | 1610318 A1 | 10/1970 |
| DE | 102004048464 A1 | 4/2006 |
| DE | 102006015100 A1 | 10/2007 |
| DE | 102006015145 A1 | 10/2007 |
| DE | 102006015148 A1 | 10/2007 |
| EP | 0621020 A1 | 10/1994 |
| WO | 2013/074909 A1 | 5/2013 |

OTHER PUBLICATIONS

Rueger, J.M., "Orthopaede"—Subject: Bone Replacement Materials: Springer-Verlag, 1998, pp. 72-83, vol. 27, Germany.

* cited by examiner

PARTICULATE ALLOPLASTIC BONE REPLACEMENT MATERIAL, AND METHOD FOR PRODUCING A FREE-FORMED POROUS BODY

The present application is a continuation of U.S. patent application Ser. No. 15/144,143, filed May 2, 2016, which claims foreign priority benefit under 35 U.S.C. § 119 of the German Patent Application No. 10 2015 107 600.4 filing date May 13, 2015, the entire contents of which German patent application are incorporated herein by reference.

FIELD OF THE DISCLOSURE

The invention relates to an alloplastic bone replacement material. The invention also relates to a method for producing a free-formed body from an alloplastic bone replacement material.

Accordingly, a subject of the invention is an alloplastic bone replacement material intended for filling and stabilising bone cavities. Moreover, a method for producing a free-formed porous body is proposed.

BACKGROUND OF THE DISCLOSURE

Bone replacement materials have been known for a long time and are used extensively in clinical applications (J. M. Rueger: Knochenersatzmittel, Orthopäde 27 (1998) 72-79.). The bone replacement materials used thus far are generally stable in volume, but not stable in shape. One notable exception is a bone replacement material that is distributed by the name of "Trabecular Metal™" by Zimmer and is known, for example from WO 2013/074 909 A1. Said material has a porous structure made to imitate the structure of human cancellous bone (sponge tissue). Said material consists of tantalum and is commercial in defined shapes and sizes. The material cannot be changed in shape and size in a surgical theatre. It cannot be processed with conventional tools in a surgical theatre. Therefore, the individual anatomical situation of the patient can be taken into account only to a limited degree. The medical user is left to attempt to adapt the implant bed to the given geometry or to insert an approximately fitting implant and to close the existing gaps with allogenic bone material or other volume fillers.

SUMMARY OF THE DISCLOSURE

Accordingly, it is the object of the invention to overcome the disadvantages of the prior art. Specifically, a bone replacement material is to be developed that can be free-formed and, once it is formed, forms a shape-stable porous body without requiring chemical curing reactions, such as, for example, radical polymerisations. The bone replacement material is to possess open porosity and is to be mechanically stable after the forming process. In this context, the porosity and the size of the pores shall be sufficient and appropriate such that human bone of a patient treated with the bone replacement material can grow into the pores. Another aim is to have the bone replacement material, in the formed state, be as load-bearing as possible. Moreover, the bone replacement material must be biocompatible such that it can be inserted into the body of a patient.

The objects of the invention are met by a particulate alloplastic bone replacement material comprising a multitude of particles, whereby the particles comprise a core and at least six pins extending from the core, whereby the pins each comprise at least one connecting element, and whereby the pins are deformable elastically such that, upon multiple particles being pressed together, the connecting elements of different particles interlock with and/or snap into each other and the particles that are interlocked with and/or snapped into each other form an open-pored body of particles that are interlocked with and/or snapped into each other.

Interlocking means that projections of the connecting elements of the pins of the particles engage projections, gripping surfaces or undercuts of connecting elements on pins of neighbouring particles such that the pins then are still mobile with respect to each other by pressing the particles further together, but can no longer be readily separated from each other. Snapping-in means that the connecting elements of the pins of the particles appropriately engage connecting elements of pins of neighbouring particles such that the particles can no longer be readily separated from each other, but can also no longer be moved towards each other by moving the particles further without a deformation of the particles occurring. Accordingly, the connecting elements can be provided by means of hooks, grooves, undercuts, snap-in means and/or opposite snap-in means and/or by hooks, grooves, undercuts and/or snap-in elements.

According to the invention, the particles that are interlocked with and/or snapped into each other and/or the three-dimensional body thus formed is/are preferred to be osteoconductive.

The invention can provide the connecting elements to be mushrooms, hooks, undercuts and/or snap-in elements, preferably mushrooms, hooks, undercuts, snap-in means and/or opposite snap-in means.

Said connecting elements are particularly well-suited for mutual snapping-in and/or interlocking. Textile connecting elements, such as hook and loop fasteners with easily deformable fibers, however, are not suitable according to the invention, since no dimensionally stable and pressure-resistant bodies can be built up by them.

The invention can also provide the distance between the connecting elements and the core of the particles to be between 0.25 mm and 2 mm, preferably to be between 0.5 mm and 1 mm.

The invention can preferably provide the particles to be spherical.

In the scope of the present invention, a particle shall be considered to be spherical if the ends of the pins are arranged on a sphere. Accordingly, for example if the particles have icosahedral symmetry, the tips of the pins of said particles are all arranged in a spherical surface. In the scope of the present invention, spherical particles do not necessarily have to be geometrically perfect spheres, but may deviate from spherical shape. Preferred spherical powder particles comprise a rounded, at least approximately spherical shape and have a ratio of the longest cross-section to the shortest cross-section of no more than 2 to 1. In the scope of the present invention, spherical geometry therefore does not refer strictly to a geometrical and/or mathematical sphere. In this context, the cross-sections refer to extreme dimensions extending within the powder particles. Particularly preferred spherical powder particles can have a ratio of the longest cross-section to the shortest cross-section of no more than 1.5 to 1 or can be spherical in shape, which is even more particularly preferred. According to the invention, diameter shall be understood to refer to the largest cross-section of the powder particles including the connecting elements in the absence of elastic deformation. In any case, the pins deviate from spherical geometry.

Preferred particles according to the invention can also be characterised in that the pins of the particles extend radially away from the core.

As a result, the particles are particularly easy to connect to each other later on.

The invention also proposes that the connecting elements can be provided at the jacket surface of the pins.

As a result, a stable connection of the pins and thus of the particles to each other can be attained.

The invention also proposes that the particles, which are pressed into each other, interlock with and/or snap into each other irreversibly.

This ensures that no particles of the fully formed bone replacement material detach from the body thus formed. This prevents irritation of the treated body at the site of treatment.

Moreover, the invention can provide the particles to have a maximal cross-section of no more than 10 mm, preferably to have a maximal cross-section between 0.5 mm and 10 mm, particularly preferably to have a maximal cross-section between 1 mm and 4 mm.

The connecting elements belong to the particles and thus contribute to the maximal cross-section of the particles. In this context, the maximal cross-section is corresponds to the length of the longest straight line that can be arranged within the geometrical shape of the particles. As a result, sufficiently fine structures can be generated. However, simultaneously, the production of the particles should not be too resource-consuming and expensive.

Moreover, the invention can provide the particles to be produced with a generative 3D printing method.

As a result, the particles, and thus the bone replacement material, can be produced inexpensively.

According to a refinement, the present invention can provide at least one of the at least one connecting elements per pin to have a truncated cone shape, whereby the longitudinal axes of the pins form the longitudinal axes of the cones and whereby the jacket of the cones faces toward the outer side that faces away from the core.

As a result, the particles can be connected in particularly stable manner by means of the connecting elements shaped as truncated cones. Moreover, said shaping prevents surrounding soft tissue and bone tissue from being injured after the implantation of the bone replacement material.

Moreover, the invention can preferably provide at least one of the at least one connecting elements per pin in the form of a hook or as a mushroom head.

The hooks and/or the mushroom heads provide for stable and non-detachable connection of the particles to each other. If the connecting elements are mushroom head-shaped, they can possess, for example, a collar at the mushroom head edge that is provided in the direction of the core such that hook-shaped connecting elements of other particles can engage said undercut, whereby an irreversible, non-detachable interlocked or snapped-in connection between the particles is produced. It is also feasible, and preferred according to the invention, that at least one particle contains various connecting elements or various pins with different connecting elements. Accordingly, one particle can simultaneously possess hooks and mushroom heads as connecting elements, both on the same pin and on different pins.

In a preferred embodiment, the connecting elements are provided as mushroom heads. In a particularly preferred embodiment, the mushroom heads are shaped appropriately such that the mushroom heads comprise a conical undercut on the side facing the core. As a result, hook-shaped snap-in elements can be interlocked irreversibly and non-detachably with said mushroom heads. If the shapes of the undercuts and of the mushroom heads match properly, further propulsion of the mushroom heads can be prevented such that the mushroom heads snap-into the undercuts.

A refinement of the present invention proposes the pins to contain a circumferential groove as additional connecting element between the core and at least one of the at least one connecting elements, whereby connecting elements of other particles can interlock with or snap into said groove, preferably snap-in appropriately such that no further motion of the connecting elements along the pins is possible.

This also facilitates particularly stable connection of particles. Moreover, it is advantageous in this context that this attains defined and unoccupied hollow spaces after snap-in connection of the particles in the body thus formed from the bone replacement material. Namely, further closure of the open pore structure by further propulsion of the pins between the pins of a neighboring particle is prevented and the pores are thus kept open.

A variant of the present invention proposes at least two connecting elements to be arranged in succession on the jacket surface of the pins, particularly preferably at least three connecting elements to be arranged in succession on the jacket surface of the pins.

As a result, the particles can be interlocked and/or snapped-in at different distances from each other. This attains higher flexibility during the forming of the bone replacement material.

Moreover, the invention can provide the particles to be sphere-shaped, bean-shaped, cuboid-shaped, cube-shaped and/or polyhedral, preferably having cubic, octahedral, dodecahedral, icosahedral and/or triacontahedral symmetry.

Based on these symmetries, stable bodies of any shape can be formed from the bone replacement material. In this context, the connecting means can have a shape that breaks the symmetry of the particles. Still, the corresponding symmetry is assigned to the particles.

Preferred bone replacement materials according to the invention can be characterised in that the particles have a maximal cross-section of more than 1 mm, preferably have a maximal cross-section of more than 2 mm, and particularly preferably have a maximal cross-section of more than 3 mm.

As a result, the particles can be fabricated inexpensively without micro-structuring.

Moreover, the invention can preferably provide the particles to be made from biocompatible plastic material, stainless steel, titanium, a titanium alloy, tantalum, a tantalum alloy or composites of said materials.

Said materials are particularly well-suited for medical purposes and these materials can be used to attain the suitable elastic properties of the pins. It is preferred, according to the invention, to produce particles consisting of metal or metal alloys by selective laser sintering or by melting with electron beams, preferably by a 3D printing method.

The biocompatible plastic material can be biodegradable. Polylactides, polyglycolides, polycaprolactones and polyester formed from different α-hydroxy carboxylic acids can be used for this purpose. Conceivable non-biodegradable plastic materials include polyamides, polyimides, polyetherketone, and polysulfone. Particles, in particular at spherical particles, made of these non-biodegradable and biodegradable plastic materials can be produced by selective laser sintering According to a refinement, the present invention can provide neighbouring pins of a particle to be situated at an appropriate distance from each other such that the pins of the particle, after elastic deformation due to interlocking and/or snapping into a connecting element of another particle, enable at least two interlocks and/or snap-in connections to two other particles, preferably enable at least three interlocks and/or snap-in connections to three other particles, particularly preferably enable more than three interlocks and/or snap-in connections to more than three other particles.

Multiple interlocking and/or snap-in connection of the particles allows a particularly stable body to be formed from the bone replacement material.

Preferably, the invention can provide the particles to be suspended in an aqueous or non-aqueous solution of biocompatible polymers and/or oligomers, and the particles and the solution, together, to form a pasty mass.

By this means, the bone replacement material can be processed particularly easily. Moreover, the solution can contain other substances that are helpful for treatment. Hyaluronic acid, hydroxyethyl starch, hydroxyethylcellulose, methylcellulose, carboxymethylcellulose, oxidised cellulose, and cellulose sulfate can be used as biocompatible polymers. Moreover, the use of gelatin as biocompatible polymer is feasible as well. In addition, the use of water-soluble polymethacrylic acid derivatives is feasible just as well. Polyvinyl alcohol and polyvinyl pyrrolidone can be used just as well.

Alternatively, the invention can provide the particles to be suspended in a low-molecular liquid that is hydrophobic at room temperature, and the particles and the liquid, together, to form a pasty mass.

By means of these two alternatives, the bone replacement material can be processed particularly easily. Moreover, the solution and/or the liquid can contain other substances that are helpful for treatment. Polyethylene glycol with a molar mass of less than 1,000 g/mol, glycerol fatty acid esters, methyl, ethyl, and isopropyl esters of fatty acids are conceivable as hydrophobic low-molecular liquids.

Moreover, the invention proposes the particles to be mixed with inorganic or organic particulate bone replacement material and/or autologous or, also, allogenic cancellous bone.

This allows the bone healing and the connection of the bone replacement material to the bone to be accelerated.

A refinement proposes the particles to be suspended in a biocompatible liquid that contains one or more pharmaceutical agents, whereby the pharmaceutical agent or agents is/are suspended and/or dissolved in the liquid.

As a result, the bone replacement material has a pharmacological effect that contributes to the healing of the patient treated with the bone replacement material. Preferred pharmaceutical agents from the group of antibiotics are, in particular, gentamicin, tobramycin, amikacin, vancomycin, teicoplanin, clindamycin, and daptomycin.

Preferably, the invention can just as well provide the particles to be coated with one or more pharmaceutical agents from the groups of antibiotics, bisphosphonates, steroids, non-steroidal anti-inflammatory drugs, growth factors, and cytostatic agents.

Again, as a result, the bone replacement material has a pharmacological effect that contributes to the healing of the patient treated with the bone replacement material. Preferred agents from the group of antibiotics are, in particular, gentamicin, tobramycin, amikacin, vancomycin, teicoplanin, clindamycin, and daptomycin.

Particularly preferred embodiments can be characterized in that the particles comprise at least fourteen pins extending from the core, preferably at least twenty pins extending from the core, particularly preferably between twenty and fifty pins extending from the core, even more particularly preferably between thirty and forty pins extending from the core.

The number of gaps, and thus of connection options between the particles, increases along with the number of pins extending from the core, particularly of pins extending radially from the core.

Moreover, the invention can provide the pores of the open-pored body formed from the particles to be interconnecting and osteoconductive, whereby the pores preferably have a free cross-section between 0.1 mm and 1 mm, particularly preferably between 0.25 mm and 0.9 mm.

This ensures that the bone can grow well into the pores of the body formed from the bone replacement material.

According to a particularly preferred refinement, the present invention can provide the bone replacement material to comprise at least one plate aside from the particles, whereby the at least one plate comprises a planar structure and a plurality of pins extending out of the planar structure of the at least one plate, whereby the pins each comprise at least one connecting element that is designed in analogous manner to the connecting elements of the particles such that the particles and the at least one plate interlock with and/or snap into each other by pressing the connecting elements of various plates and particles onto each other, and whereby the plates and particles that are interlocked with and/or snapped into each other form an open-pored body of plates and particles that are interlocked with and/or snapped into each other.

As a result, an even more versatile bone replacement material is attained that can be free-formed and used to bridge gaps and cavities.

The objects underlying the present invention are also met by a method for forming a body made of a particulate alloplastic bone replacement material according to the invention, in which the particles are pushed against each other, whereby the particles interlock with and/or snap into each other and form an open-pored body.

In this context, the invention can provide the particles to be contacted to each other before they are pushed against each other.

Moreover, the invention can provide that particles to be connected to a porous three-dimensional body of a second bone replacement material by snapping-in and/or interlocking the connecting elements with the pores of the second bone replacement material, and/or the particles to be connected to a planar third bone replacement material that comprises a plurality of pins having connecting elements, whereby, preferably, the pins and the connecting elements of the planar third bone replacement material comprise the features of the pins and connecting elements of the particles of the bone replacement material according to the invention.

The porous three-dimensional body of the second bone replacement material can, for example, be a Trabecular Metal™ made by Zimmer.

And lastly, the underlying objects of the invention are also met through the use of the alloplastic bone replacement material according to the invention as implant material in trauma surgery, orthopaedics or veterinary medicine.

According to the invention, the (preferably spherical) particles of the bone replacement material contacting each other form a mechanically stable composite upon exposure to a pressure.

The invention is based on finding, surprisingly, that particles that snap-in and/or interlock mechanically can be used as alloplastic bone replacement material. In this context, the particles can be made to have a desired shape and can be snapped into each other by applying pressure and can thus be connected to each other. Based on a suitable shape of the particles, a porous bone replacement material that is mechanically sufficiently stable for medical application is thus formed. The bone can grow into the pores of the bone replacement material connected by pressure and can thus become connected permanently to the bone replacement material.

It has been found, surprisingly, that the bone replacement material according to the invention can be inserted, in the form of particles, in cavities of any shape and can be cured into a porous, but homogeneous body through interlinking of the individual spherical particles by simple compression by hand or by means of a pestle. This is advantageous as compared to the previous "Trabecular Metal™" bone replacement material, whose shape and size cannot be freely determined by the medical user. It is thus feasible to fill bone cavities of any shape with an in-situ curing and/or hardening bone replacement material without needing any chemical reactions, such as for example radical polymerisations, for this purpose. The bone replacement material according to the invention can be cured easily by simply compressing spherical particles that touch against each other.

Mechanically interlocked systems following the design principles of hook and loop fasteners have been known for several decades. The principle of the hook and loop fastener was first described by de Mestral in CH 295 638 A. Said principle has been developed further and is put to use in a wide range of reversibly closing Velcro closures. Exemplary refinements are described in the publications, DE 1 610 318 A1, DE 1 625 396 A1, U.S. Pat. Nos. 5,077,870 A, and 4,290,174 A.

An interesting refinement followed later, in which reversibly hook-and-loop-closing steel belt systems for high mechanical load applications and applications at high temperatures were developed (DE 10 2004 048 464 A1, DE 10 2006 015 100 A1, DE 10 2006 015 145 A1, DE 10 2006 015 148 A1).

In the scope of the present invention, it has been evident, surprisingly, that said systems and/or said functional principles can be used for bone replacement materials and/or can be transferred to bone replacement materials. In this context, it is advantageous for the bone replacement materials that connections of this type do not close tightly, but rather gaps remain as an open-pored structure. Bone can grow into the interconnecting pores thus formed in the solid such that the pores allow a stable connection between the bone and the bone replacement material to be generated. For this purpose, one must make sure that the pores in the bone replacement material have a sufficient free cross-section. The pores are called osteoconductive, if the bone can grow into the pores and can thus become connected to the body formed from the bone replacement material.

An exemplary embodiment of the present invention that is particularly preferred according to the invention is a particulate alloplastic bone replacement material comprising a multitude of spherical particles, whereby the particles are made of a core and at least six pins extending radially away from the core, whereby at least one snap-in element is provided on the jacket surface of each pin, and whereby the pins with the snap-in elements are made from at least one elastically deformable material. The particles are designed appropriately such that pressing the spherical particles together causes contacting spherical particles to snap into or interlock with each other irreversibly and to form an open-pored body made of spherical particles that are interlocked with or snapped into each other.

BRIEF DESCRIPTION OF THE DRAWINGS

Further exemplary embodiments of the invention shall be illustrated in the following on the basis of fourteen schematic figures, though without limiting the scope of the invention. In the figures.

DETAILED DESCRIPTION OF THE DISCLOSURE

Figure 1:
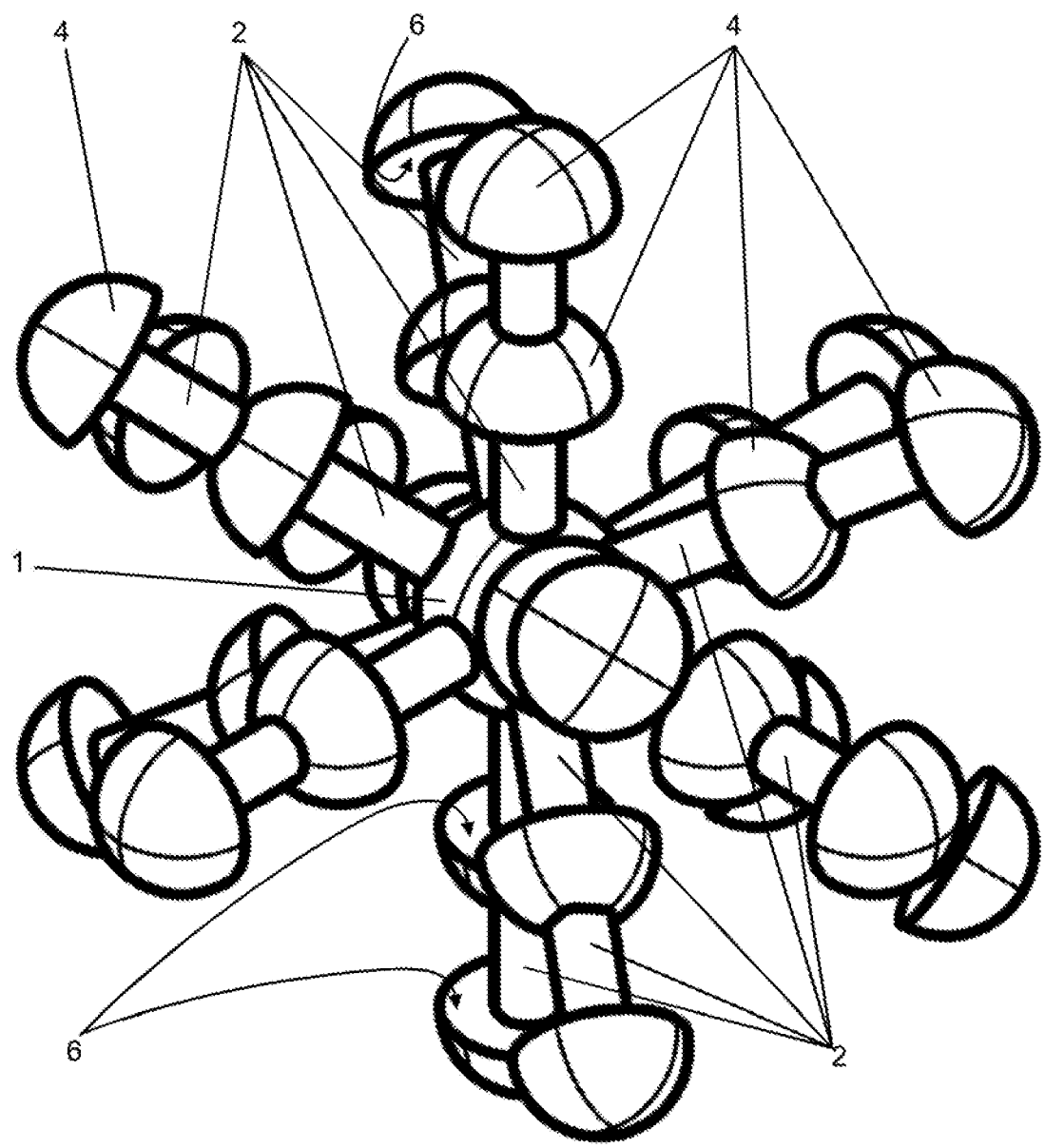
FIG. 1: shows a schematic perspective view of a particle of a bone replacement material according to the invention.
Figure 2:
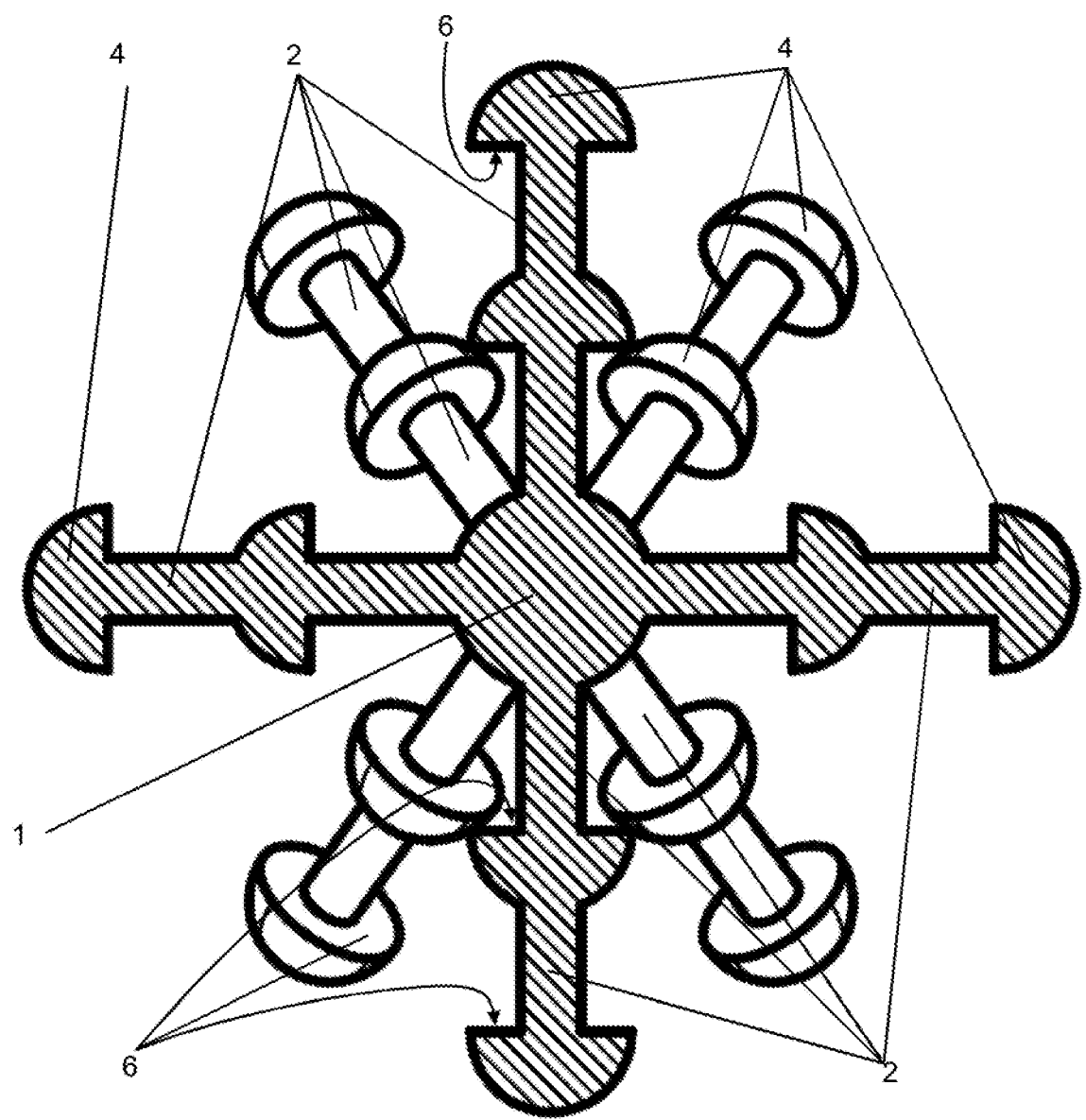
FIG. 2: shows a schematic cross-sectional view of the particle according to FIG. 1.
Figure 3:
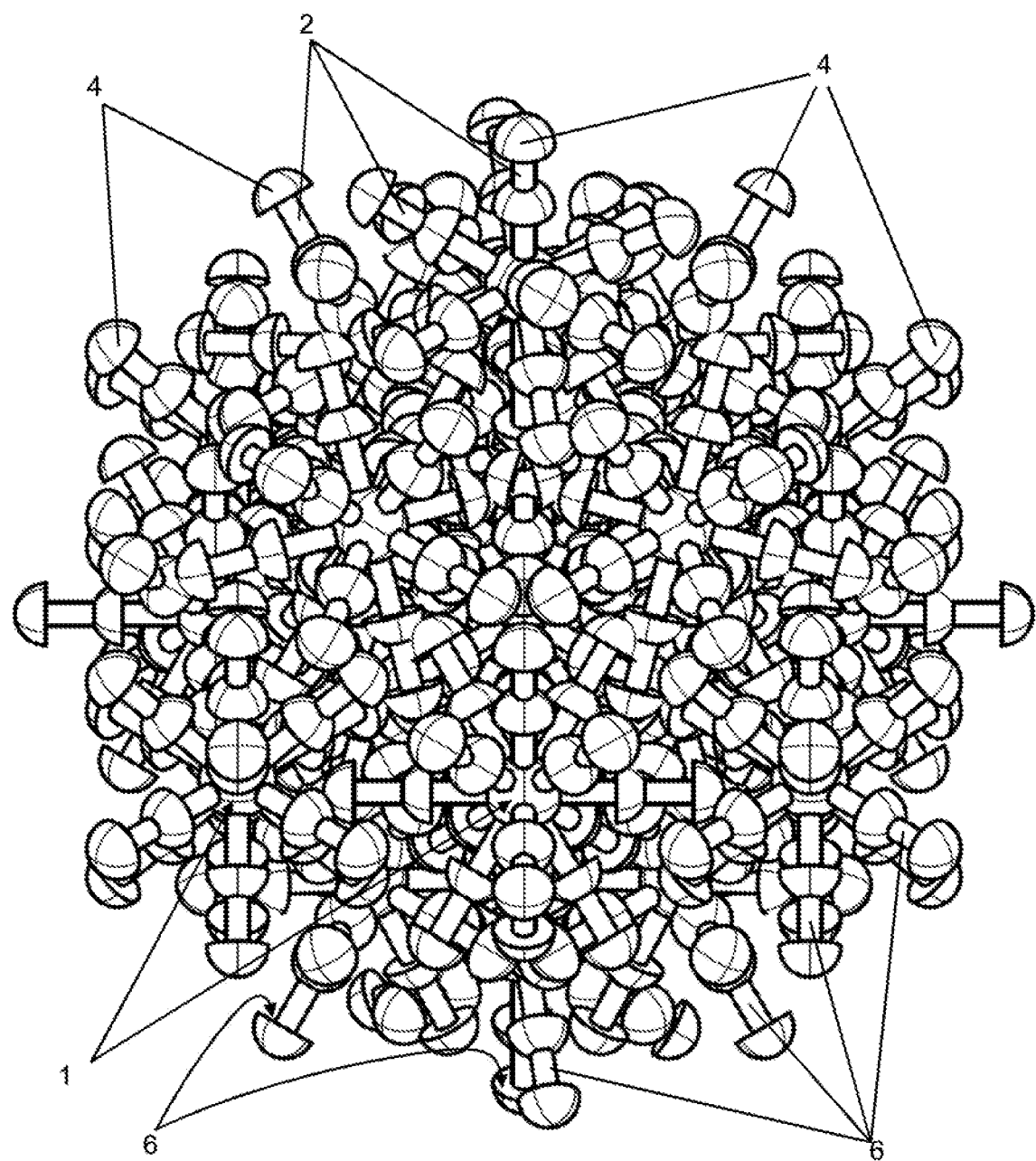
FIG. 3: shows a schematic perspective view of a bone replacement material according to the invention made of multiple particles in accordance with FIGS. 1 and 2 that are connected to each other.

FIGS. 1 and 2 show a schematic perspective view of a particle of a bone replacement material according to the invention and a schematic cross-sectional view of said particle, respectively. FIG. 3 shows a related schematic perspective view of a bone replacement material according to the invention made of multiple particles that are shown in FIGS. 1 and 2 and are connected to each other to form an open-pored body. The particles consist of an elastic biocompatible plastic material or of stainless steel, titanium, a titanium alloy, tantalum, a tantalum alloy or can also be fabricated from composites of said materials. The particles are manufactured by a CAM procedure (CAM—computer-aided manufacturing) and/or a 3D printing procedure, for example by selective laser melting SLM (selective laser melting). Other rapid prototyping methods and/or computer-aided generative production methods can also be used for producing the particles, such as, for example, Fused Layer Modeling/Manufacturing (FLM), Fused Deposition Modeling (FDM), Laminated Object Modelling (LOM) of plastic films, Layer Laminated Manufacturing (LLM) of plastic films, Electron Beam Melting (EBM) of plastic materials or metals, Multi Jet Modeling (MJM) of plastic materials, Selective Laser Sintering (SLS) of plastic materials or metals, Stereolithography (STL or SLA) of plastic materials, polishing or multi-axes milling procedures or Digital Light Processing (DLP) of photopolymerising liquid plastic materials.

The particles are composed of a core 1 that is arranged in the geometrical centre of the particle as well as fourteen pins 2 that extend radially away from the core 1 in various directions. The pins 2 each have two mushrooms 4 (or mushroom heads 4) connected to the otherwise cylindrical pins 2 as connecting elements. The mushrooms 4 are rounded towards the outside (away from the core 1) and form spherical segments. However, other types of rounding, such as, for example, ellipsoidal segments, are feasible just as well. On the side oriented towards the core 1, the mushrooms 4 form a planar gripping surface 6 that is suitable for interlocking with other mushrooms 4 of engaging particles. Preferably, the mushrooms 4 have a slightly larger diameter than the one shown in FIGS. 1 to 3 to allow them to engage and interlock with each other more easily.

In order to form a bone replacement material according to the invention, the particles preferably are situated to touch against each other, without being interlocked, such that the mushrooms 4 of the pins 2 do not engage each other yet. Moreover, the particles can be present in the form of a slurry, in which they are mixed with a liquid. The liquid preferably contains at least one pharmaceutically active substance suitable for controlling an infection or for stimulating bone growth. Alternatively or in addition, the particles can be coated with a pharmaceutically active substance of this type.

The bone replacement material can be formed by pushing the particles into each other. By this means, the particles interlock with or snap into each other and the bone replacement material becomes reinforced as desired. In this context, the particles become appropriately connected to each other such that free gaps remain between the particles that are connected to each other such that the three-dimensional body formed from the particles is open-pored. The particles have a diameter of approximately 5 mm such that the remaining pores have a free cross-section in the range of approximately 0.5 mm. Said cross-section is still sufficient to allow bone material to be formed in and/or to grow into the pores. The body with its open pores can therefore be called osteoconductive. The three-dimensional body formed from the particles is therefore well-suited as bone replacement material.

The particles should be pushed firmly into each other such that the three-dimensional body is dimensionally stable. In this context, the particles snap into each other by the mushrooms 4 elastically deforming the pins 2 of connected particles and by the mushrooms 4 of neighbouring particles being pulled toward the core 1 by the elastic restoring force of the pins 2. It is feasible just as well that the edges of the mushrooms 4 plastically deform the pins 2 or the mushrooms 4 of neighbouring particles to a small extent and that the particles are thus snapped into each other.

Figure 4:
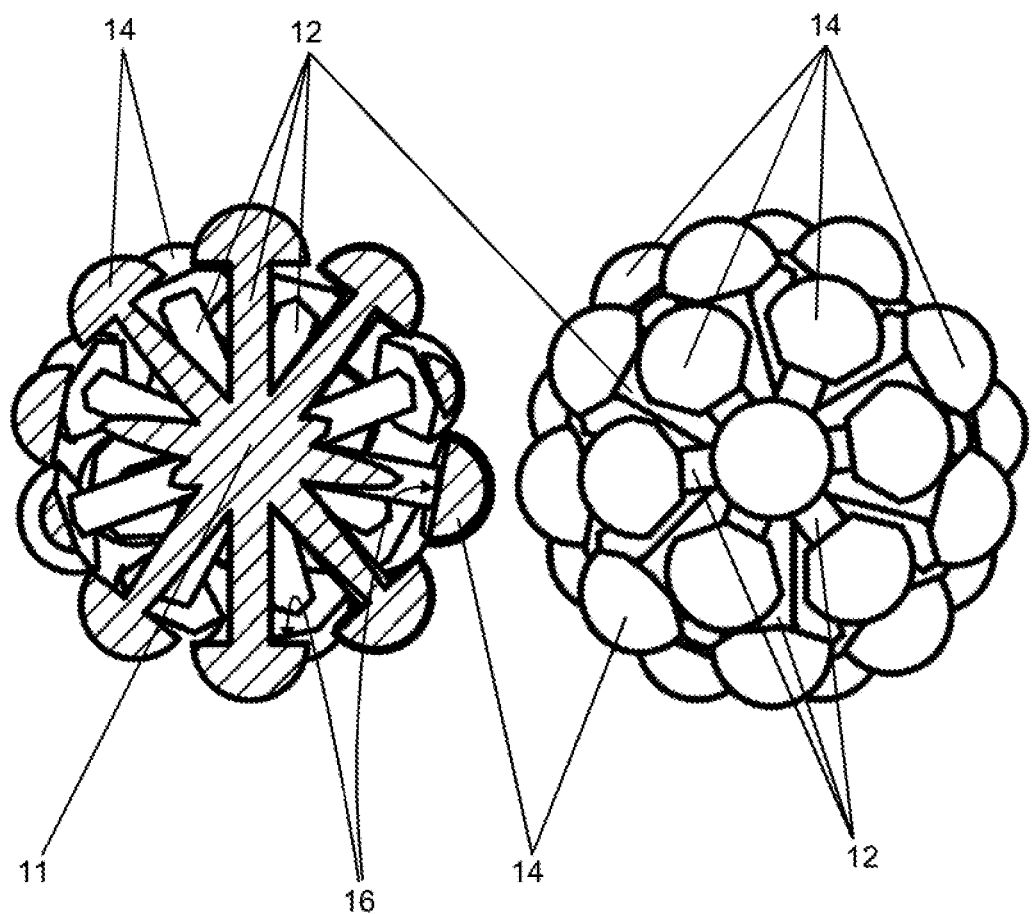
FIG. 4: shows a schematic cross-sectional view (left) and schematic perspective view (right) of two particles of a second alternative bone replacement material according to the invention.
Figure 5:
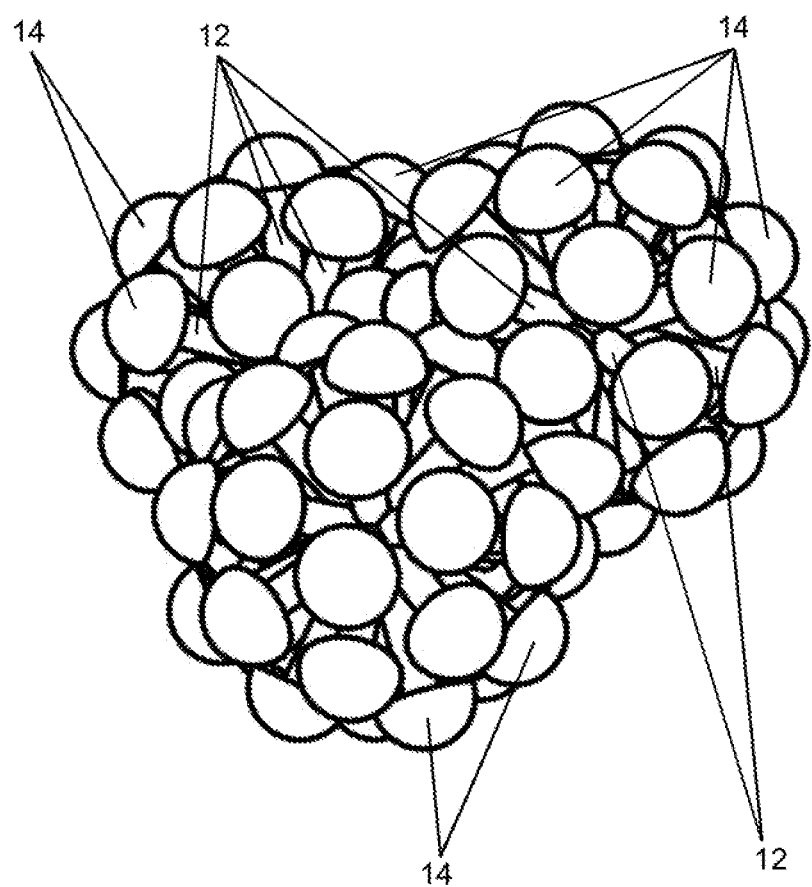
FIG. 5: shows a schematic perspective view of three particles of the second bone replacement material according to the invention according to FIG. 4 that are not connected to each other.

FIG. 4 shows a schematic cross-sectional view (left) and a schematic perspective view (right) of two particles of a second alternative bone replacement material according to the invention and FIG. 5 shows a schematic perspective view of three particles of the second bone replacement material according to the invention according to FIG. 4 that are connected to each other and are connected to each other to form an open-pored body. The particles consist of stainless steel, titanium, a titanium alloy, tantalum and/or a tantalum alloy or can be fabricated from composites of said materials or a biocompatible plastic material. The particles are produced through a CAM procedure and/or a 3D printing procedure, for example through selective electron beam melting. Other rapid prototyping methods can also be used for producing the particles.

The particles are composed of a core 11 that is arranged in the geometrical centre of the particle as well as thirty two pins 12 that extend radially away from the core 11 in various directions. The pins 12 each have one mushroom 14 connected to the otherwise cylindrical pins 12 as connecting elements. The mushrooms 14 are rounded towards the outside (away from the core 11) and form spherical segments. However, other types of rounding, such as, for example, ellipsoidal segments, are feasible just as well. On the side oriented towards the core 11, the mushrooms 14 form a planar gripping surface 16 that is suitable for interlocking with other mushrooms 14 of engaging particles.

In order to form a bone replacement material according to the invention, the particles preferably are situated to touch against each other, without being interlocked, such that the mushrooms 14 of the pins 12 do not engage each other yet. Moreover, the particles can be present in the form of a slurry, in which they are mixed with a liquid. The liquid preferably contains at least one pharmaceutically active substance suitable for controlling an infection or for stimulating bone growth. Alternatively or in addition, the particles can be coated with a pharmaceutically active substance of this type.

The bone replacement material can be formed by pushing the particles into each other. By this means, the particles interlock with or snap into each other and the bone replacement material becomes reinforced as desired. In this context, the particles become appropriately connected to each other such that free gaps remain between the particles that are connected to each other such that the three-dimensional body formed from the particles is open-pored. The particles have a diameter of approximately 3 mm such that the remaining pores have a free cross-section in the range of approximately 0.3 mm. Said cross-section is still sufficient to allow bone material to be formed in and/or to grow into the pores. The body with its open pores can therefore be called osteoconductive. The three-dimensional body formed from the particles is therefore well-suited as bone replacement material.

The particles should be pushed firmly into each other such that the three-dimensional body is dimensionally stable. In this context, the particles snap into each other by the mushrooms 14 elastically deforming the pins 12 of connected particles and by the mushrooms 14 of neighbouring particles being pulled toward the core 11 by the elastic restoring force of the pins 12. It is feasible just as well that the edges of the mushrooms 14 plastically deform the pins 12 or the mushrooms 14 of neighbouring particles to a small extent and that the particles are thus snapped into each other.

Figure 6:
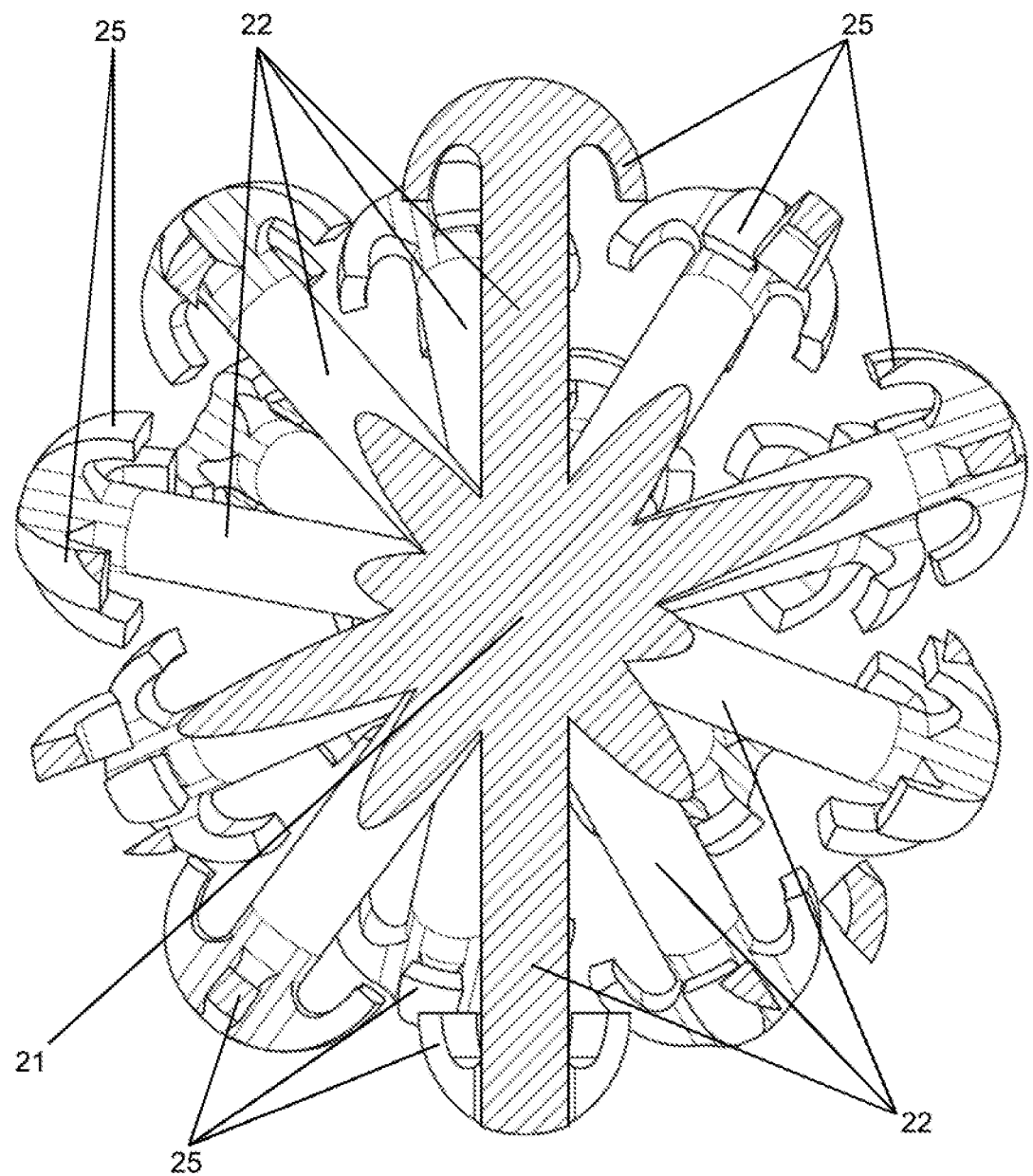
FIG. 6: shows a schematic sectioned view of a particle of a third alternative bone replacement material according to the invention.
Figure 7:
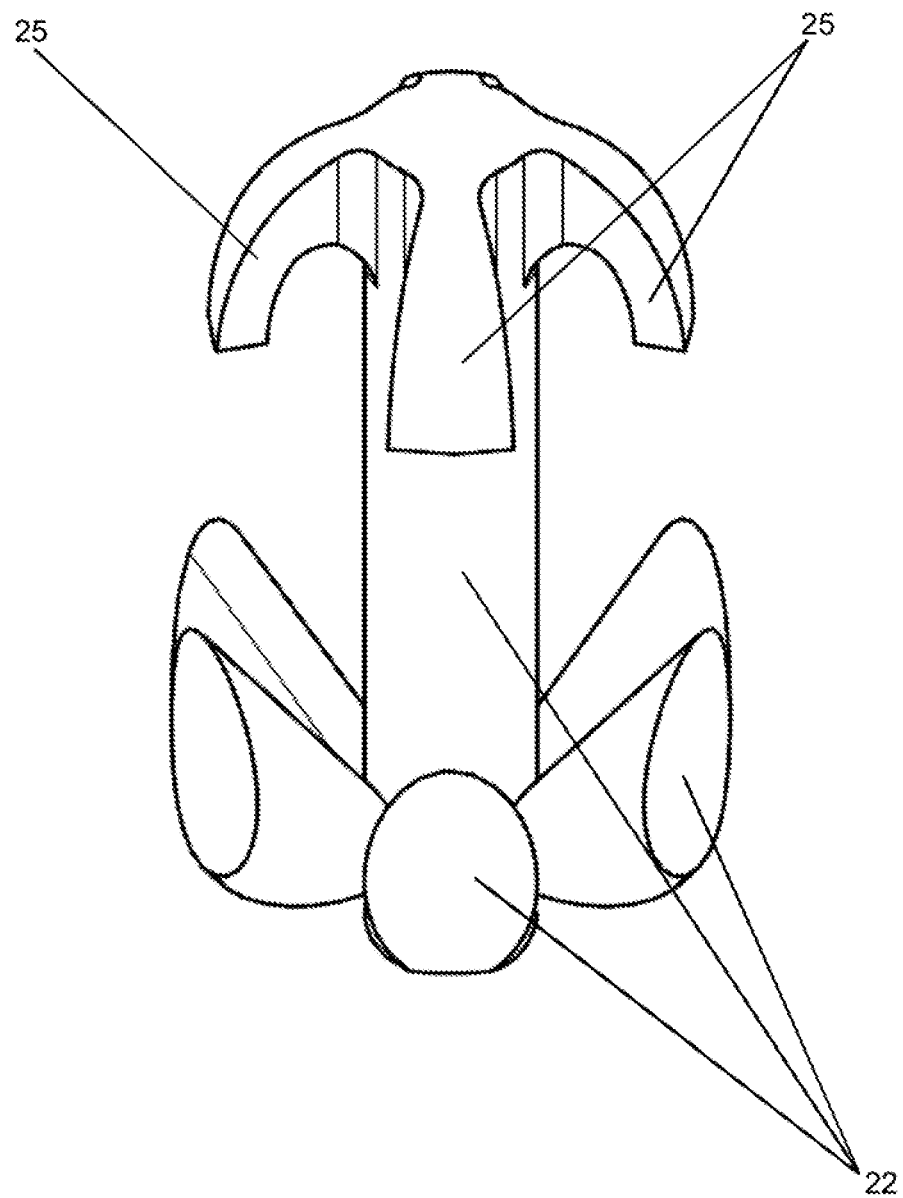
FIG. 7: shows a schematic perspective view of a detail of the particle according to FIG. 6.
Figure 8:
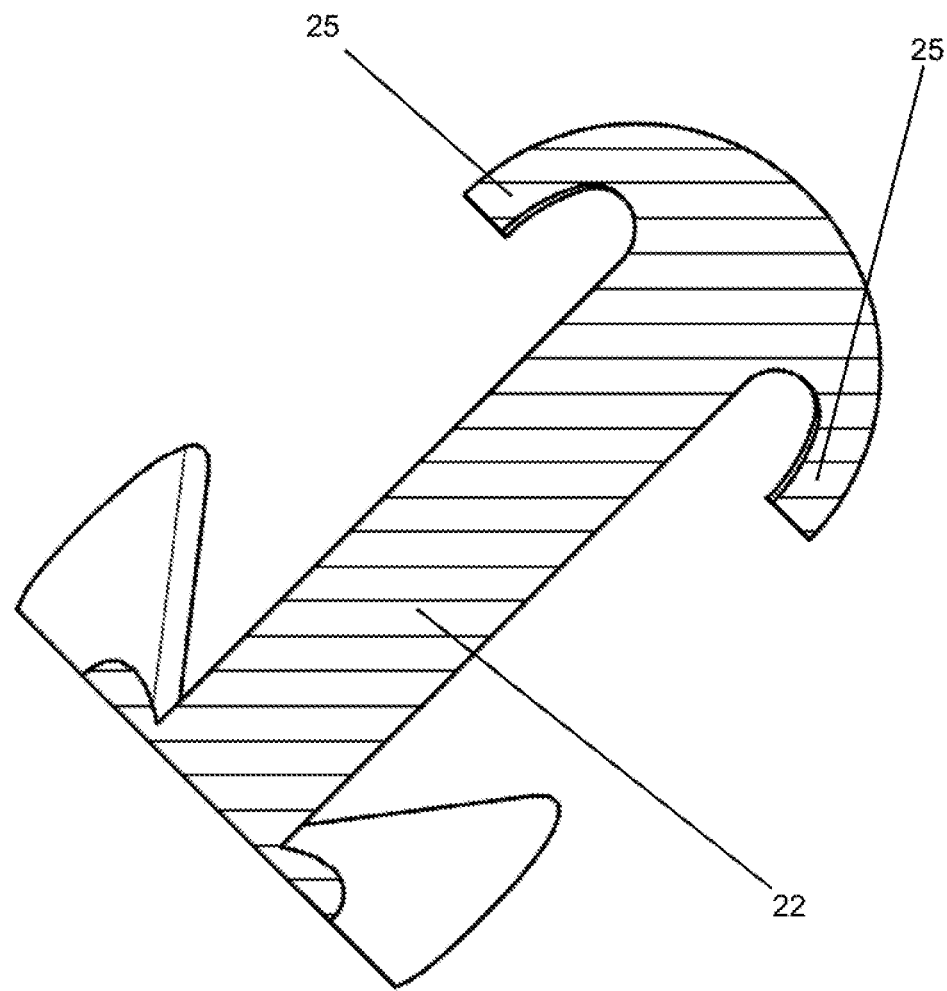
FIG. 8: shows a schematic cross-sectional view of a detail of the particle according to FIG. 6.
Figure 9:
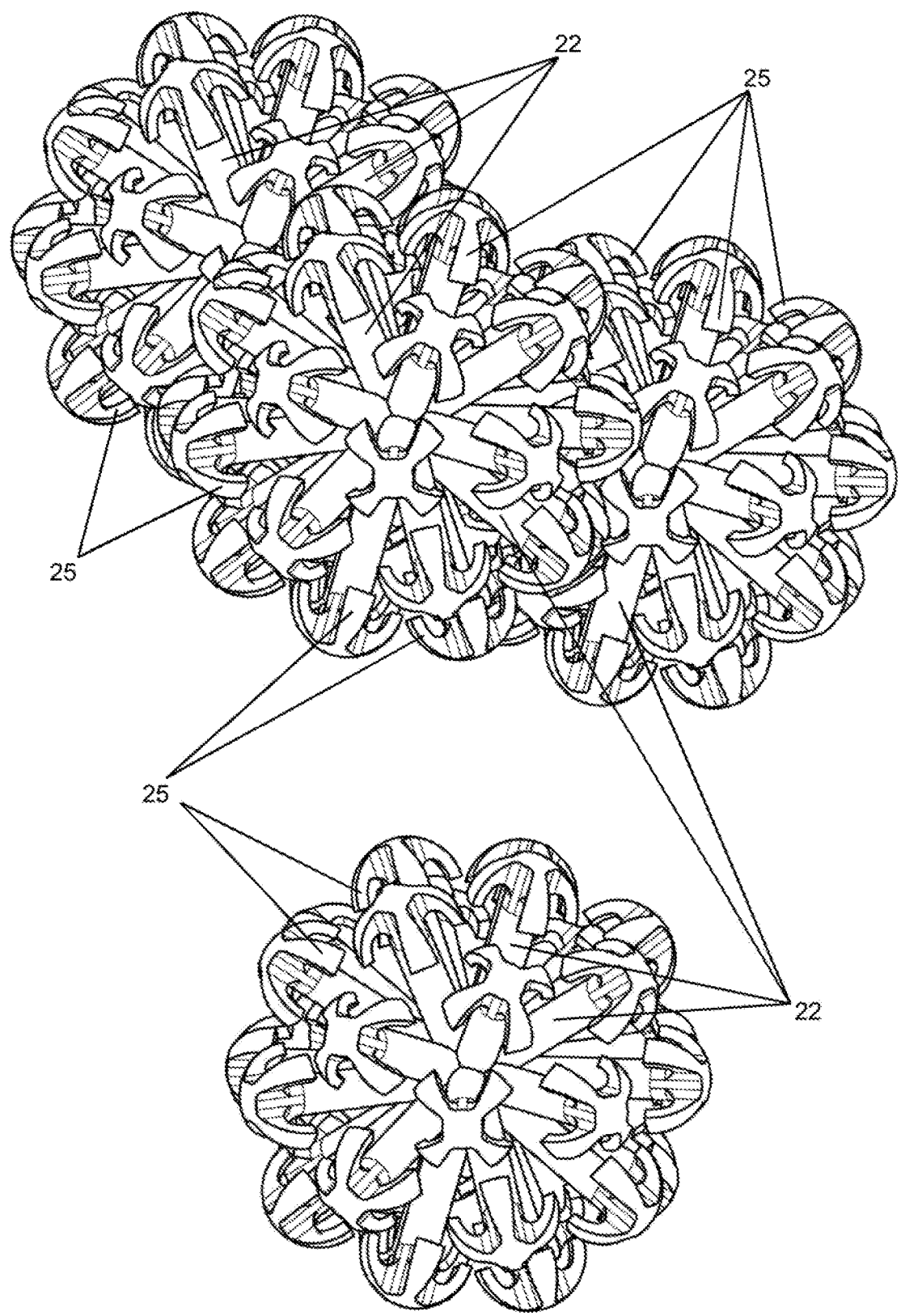
FIG. 9: shows a schematic perspective view of four particles according to FIG. 6, three of which are connected to each other.

FIG. 6 shows a schematic sectioned view of a particle of a third alternative bone replacement material according to the invention, FIG. 7 shows a schematic perspective view of a detail of the particle according to FIG. 6, FIG. 8 shows a schematic cross-sectional view of a detail of the particle according to FIG. 6, and FIG. 9 shows a schematic perspective view of four particles according to FIG. 6, three of which are connected to each other to form an open-pored body. The particles consist of tantalum or a tantalum alloy, but can just as well be fabricated from other biocompatible metals or biocompatible metal alloys or a biocompatible plastic material. The particles are produced through a CAM procedure and/or a 3D printing procedure, for example through selective electron beam melting. Other rapid prototyping methods can also be used for producing the particles.

The particles are composed of a core 21 that is arranged in the geometrical centre of the particle as well as thirty two pins 22 that extend radially away from the core 21 in various directions. The pins 22 each have a group of four hooks 25 connected to the otherwise cylindrical pins 22 as connecting elements. The hooks 25 are spherically rounded towards the outside (away from the core 21). Other types of rounding, such as, for example, ellipsoidal segments, are feasible just as well. On the side oriented towards the core 21, the hooks 25 undercuts that are suitable for interlocking with other hooks 25 of engaging particles.

In order to form a bone replacement material according to the invention, the particles preferably are situated to touch against each other, without being interlocked, such that the hooks 25 of the pins 22 do not engage each other yet. Moreover, the particles can be present in the form of a slurry, in which they are mixed with a liquid. The liquid preferably contains at least one pharmaceutically active substance suitable for controlling an infection or for stimulating bone growth. Alternatively or in addition, the particles can be coated with a pharmaceutically active substance of this type.

The bone replacement material can be formed by pushing the particles into each other. By this means, the particles interlock with or snap into each other and the bone replacement material thus becomes reinforced as desired. In this context, the particles become appropriately connected to each other such that free gaps remain between the particles that are connected to each other such that the three-dimensional body formed from the particles is open-pored. The particles have a diameter of approximately 8 mm such that the remaining pores have a free cross-section in the range of approximately 0.8 mm. Said cross-section is still sufficient to allow bone material to be formed in and/or to grow into the pores. The body with its open pores can therefore be called osteoconductive. To promote the osteoconductivity, the surface of the particles can be coated with a bone growth-promoting substance. The three-dimensional body formed from the particles is therefore well-suited as bone replacement material.

The particles should be pushed firmly into each other such that the three-dimensional body is dimensionally stable. In this context, the particles snap into each other by the hooks 25 sliding between the hooks 25 of connected particles or elastically deforming the pins 22 of connected particles and by the hooks 25 of neighbouring particles being pulled toward the core 21 by the elastic restoring force of the pins 22 and hooks 25. It is feasible just as well that edges, corners or tips (not shown) of the hooks 25 plastically deform the pins 22 or hooks 25 of neighbouring particles to a small extent and that the particles are thus snapped into each other.

Figure 10:
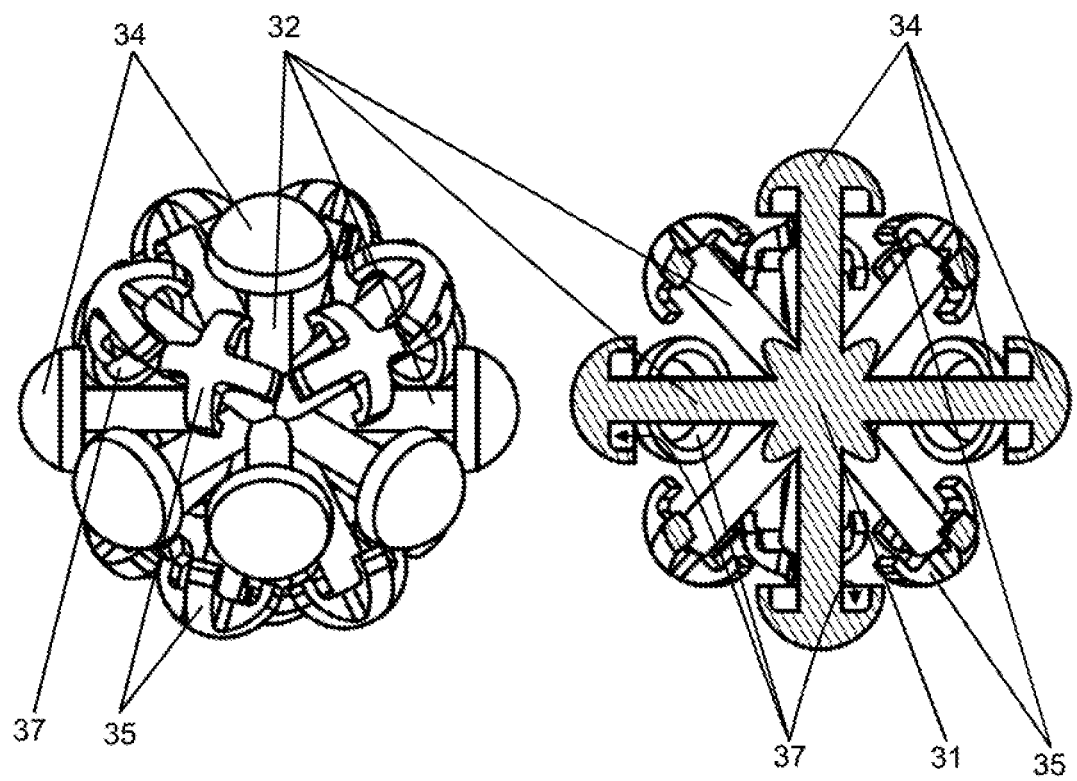
FIG. 10: shows a schematic cross-sectional view (right) and schematic perspective view (left) of two particles of a fourth alternative bone replacement material according to the invention.
Figure 11:
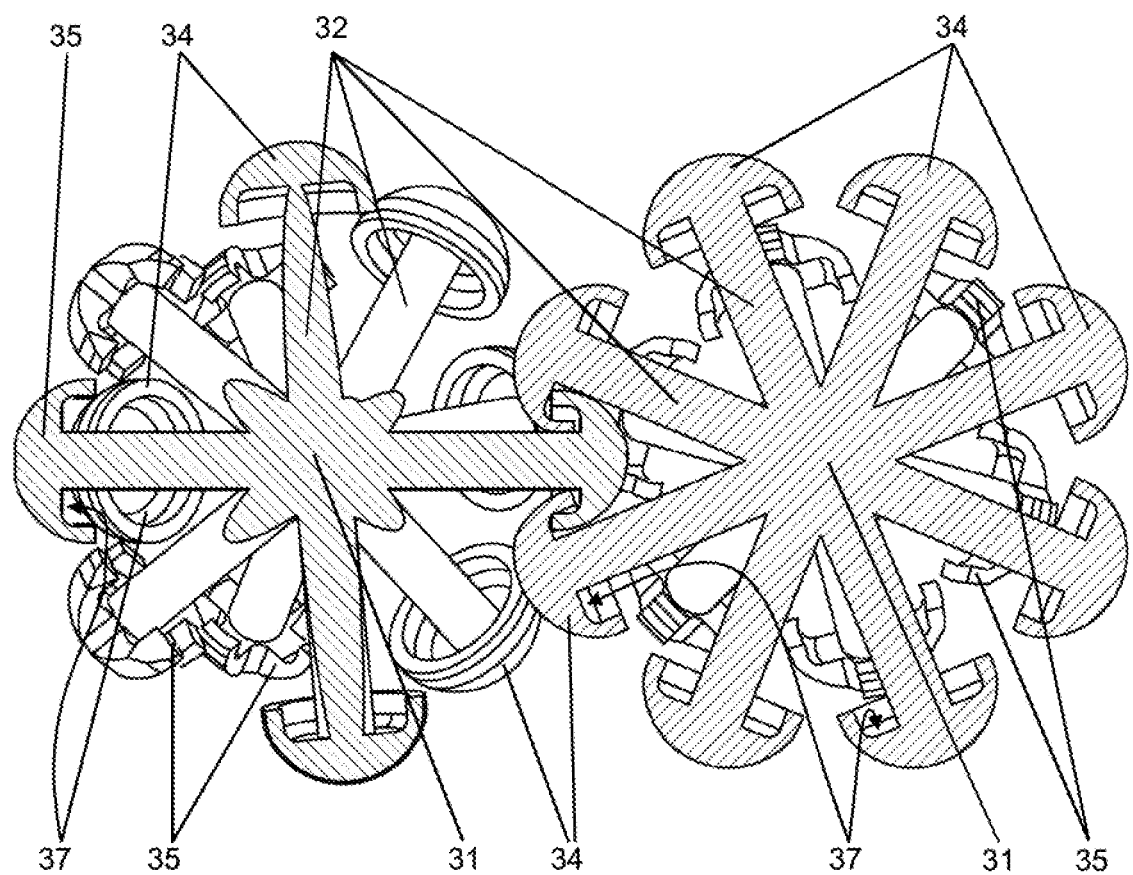
FIG. 11: shows a schematic cross-sectional view of two particles of the fourth bone replacement material according to the invention according to FIG. 10 that are connected to each other.

FIG. 10 shows a schematic cross-sectional view (right) and schematic perspective view (let) of two particles of a fourth alternative bone replacement material according to the invention. FIG. 11 shows a schematic cross-sectional view of two particles of the fourth bone replacement material according to the invention according to FIG. 10 that are connected to each other. The particles consist of tantalum or a tantalum alloy, but can just as well be fabricated from other biocompatible metals or biocompatible metal alloys or a biocompatible plastic material. The particles are produced through a CAM procedure or through a 3D printing procedure respectively. All suitable rapid prototyping methods can also be used for producing the particles.

The particles are composed of a core 31 that is arranged in the geometrical centre of the particle as well as twenty two pins 32 that extend radially away from the core 31 in various directions. Either mushrooms 34 or a group of four hooks 35 each are arranged as connecting elements on the otherwise cylindrical pins 32. Accordingly, the mushrooms 34 and the hooks 35 are shaped to be spherically rounded towards the outside (away from the core 31). Other types of rounding, such as, for example, ellipsoidal segments, are feasible just as well. The mushrooms 34 have undercuts 37 on the side oriented toward the core 31. Likewise, the hooks 35 comprise undercuts. The undercuts 37 of the mushrooms 34 and the undercuts of the hooks 35 are suitable for interlocking to other mushrooms 34 and hooks 35 of engaging particles.

In order to form a bone replacement material according to the invention, the particles preferably are situated to touch against each other, without being interlocked, such that the mushrooms 34 and hooks 35 of the pins 32 do not engage each other yet. Moreover, the particles can be present in the form of a slurry, in which they are mixed with a liquid. The liquid preferably contains at least one pharmaceutically active substance suitable for controlling an infection or for stimulating bone growth. Alternatively or in addition, the particles can be coated with a pharmaceutically active substance of this type.

The bone replacement material can be formed by pushing the particles into each other. As a result, the particles interlock with or snap into each other as shown in the schematic cross-sectional view according to FIG. 11. In this context, the hooks 35 engaged, for example, the undercuts 37 of the mushrooms 34. In order to get into this position, the pins 32 must be bent elastically towards the side by applying a mechanical pressure onto the particles to be connected. Upon elastic restoration of the pins 32, the hooks 35 are pushed into the undercuts of the neighbouring mushrooms 34 and/or into the undercuts of the neighbouring hooks 35. In the embodiment according to FIGS. 10 and 11, the lengths and diameters of the pins 32 as well as the shape of the hooks 35 and mushrooms 34 are matched to each other appropriately such that the outer curvature of the hooks 35 effects just a slight elastic deformation of the pins 32 when the tips of the hooks 35 touch against the bottom of the undercuts 37 of the connected mushrooms 34 and hooks 35. As a result, the hooks 35 snap into the mushrooms 34, since the hooks 35 and/or the mushrooms 34 cannot be pushed more deeply into each other without applying a force (i.e. without further elastic deformation of the pins 32). This is no longer possible after multiple interlocking and/or snap-in connection of the particles by multiple mushrooms 34 and/or hooks 35 of one particle and/or multiple particles to another particle. The bone replacement material is thus becoming reinforced as desired. This type of connection of the particles can be applied similarly to the other embodiments according to FIGS. 1 to 9.

In this context, the particles become appropriately connected to each other such that free gaps remain between the particles that are connected to each other such that the three-dimensional body, which is formed from the particles and becomes reinforced, is open-pored. The particles have a diameter of approximately 6 mm such that the remaining pores have a free cross-section in the range of approximately 0.6 mm. Said cross-section is still sufficient to allow bone material to be formed in and/or to grow into the pores. The body with its open pores can therefore be called osteoconductive. To promote the osteoconductivity, the surface of the particles can be coated with a bone growth-promoting substance. The three-dimensional body formed from the particles is therefore well-suited as bone replacement material.

The particles should be pushed firmly into each other such that the three-dimensional body is dimensionally stable. In this context, the particles snap into each other by the mushrooms 34 and hooks 35 sliding between the mushrooms 34 and hooks 35 of connected particles and thus deforming the pins 32 of connected particles elastically. Due to the elastic restoring force of the pins 32, the mushrooms 34 and hooks 35 can be pulled into the undercuts 37 of other mushrooms 34 and hooks 35 of neighbouring particles. It is feasible just as well that edges, corners or tips (not shown) of the hooks 35 or the edges of the mushrooms 34 plastically deform the pins 32 or the mushrooms 34 or hooks 35 of neighbouring particles to a small extent and that the particles are thus snapped into each other.

Figure 12:
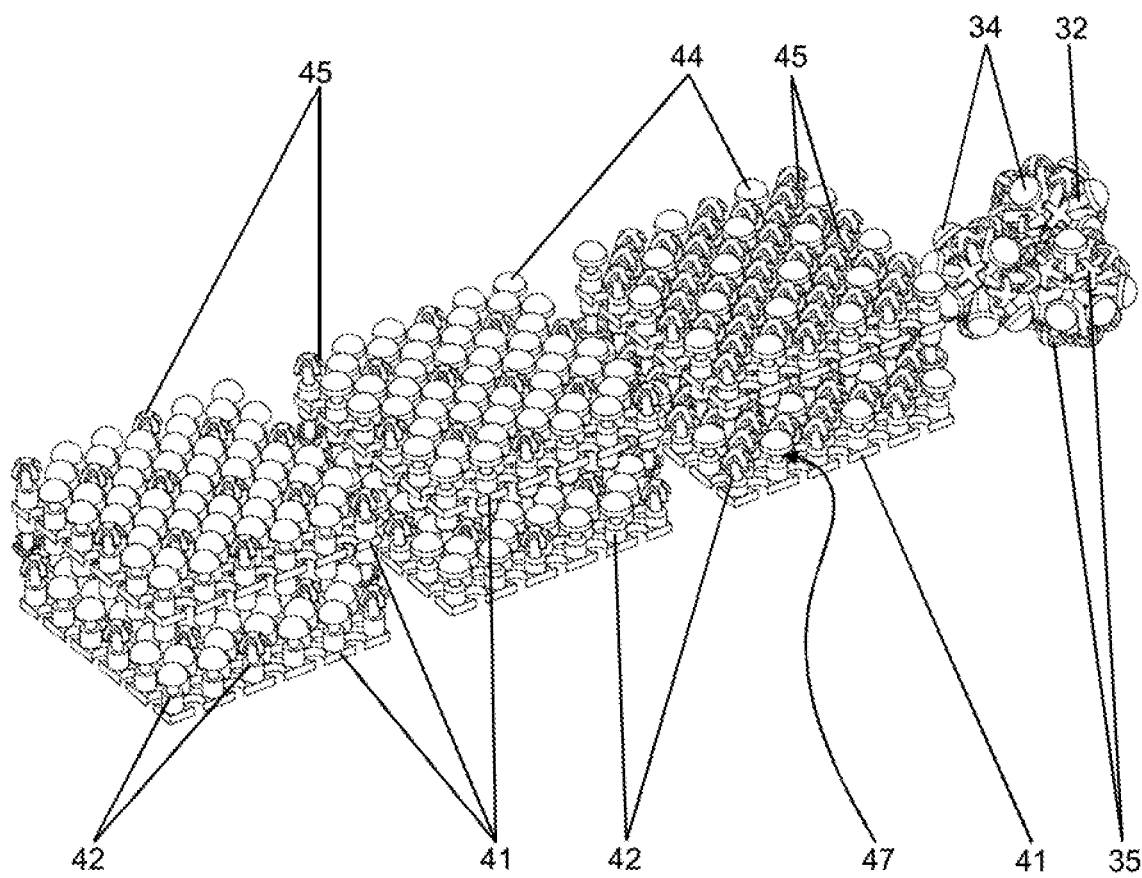
FIG. 12: shows a schematic perspective view of three particles of the fourth bone replacement material according to the invention according to FIGS. 10 and 11 that are connected to each other, and multiple plates of a bone replacement material that can be connected by means of the particles.

FIG. 12 shows a schematic perspective view of three particles of the fourth bone replacement material according to the invention according to FIG. 10 that are connected to each other, and multiple plates of a bone replacement material that can be connected by means of the particles. The plates comprise a supporting planar structure 41 comprising a multitude of perforations, whereby pins 42 are arranged between the perforations on the planar structure 41 and terminate in mushrooms 44 or in groups of four hooks 45 each as connecting elements 44, 45. The pins 42 comprising the mushrooms 44 or hooks 45 are structured analogously to the pins 32 comprising the mushrooms 34 and hooks 35 of the particles and therefore comprise circumferential grooves 47 and undercuts. Different from the pins 32 of the particles, the pins 42 do not extend radially away from a core 31, but perpendicularly away from the planar structure 41. In this context, the plates can comprise pins 42 on both sides of the planar structure 41 or just on one side of the planar structure 41.

Alternatively, the plates can comprise other pins and connecting elements like the ones described in the context of the particles of FIGS. 1 to 9. Preferably, the pins and connecting elements of the plates are matched to the pins and connecting elements of the particles to allow uniform stability to be attained. The materials from which the plates can be made can be the same as the materials of the particles and the same production procedures can be used. Due to their size (thickness approximately 1 mm to 10 mm), the plates can be deformed and adapted to the bone surface to be treated.

The plates can be connected to the bone of a patient through fastening means (not shown) in the form of tips or screws. Subsequently, further plates, or the particles of a bone replacement material according to the invention are fastened on the plates. In this context, the particles and the plates become appropriately connected to each other such that free gaps remain between the particles and plates that are connected to each other such that the reinforced three-dimensional body formed from the particles and plates is open-pored. The free cross-sections of the open pore structure must still be sufficient such that bone material can form in and/or grow into the pores.

The open-pored three-dimensional body formed from the plates and particles can also be called osteoconductive. To promote the osteoconductivity, the surface of the plates can be coated with a bone growth-promoting substance. The three-dimensional body formed from the particles and plates is therefore well-suited as bone replacement material.

Figure 13:
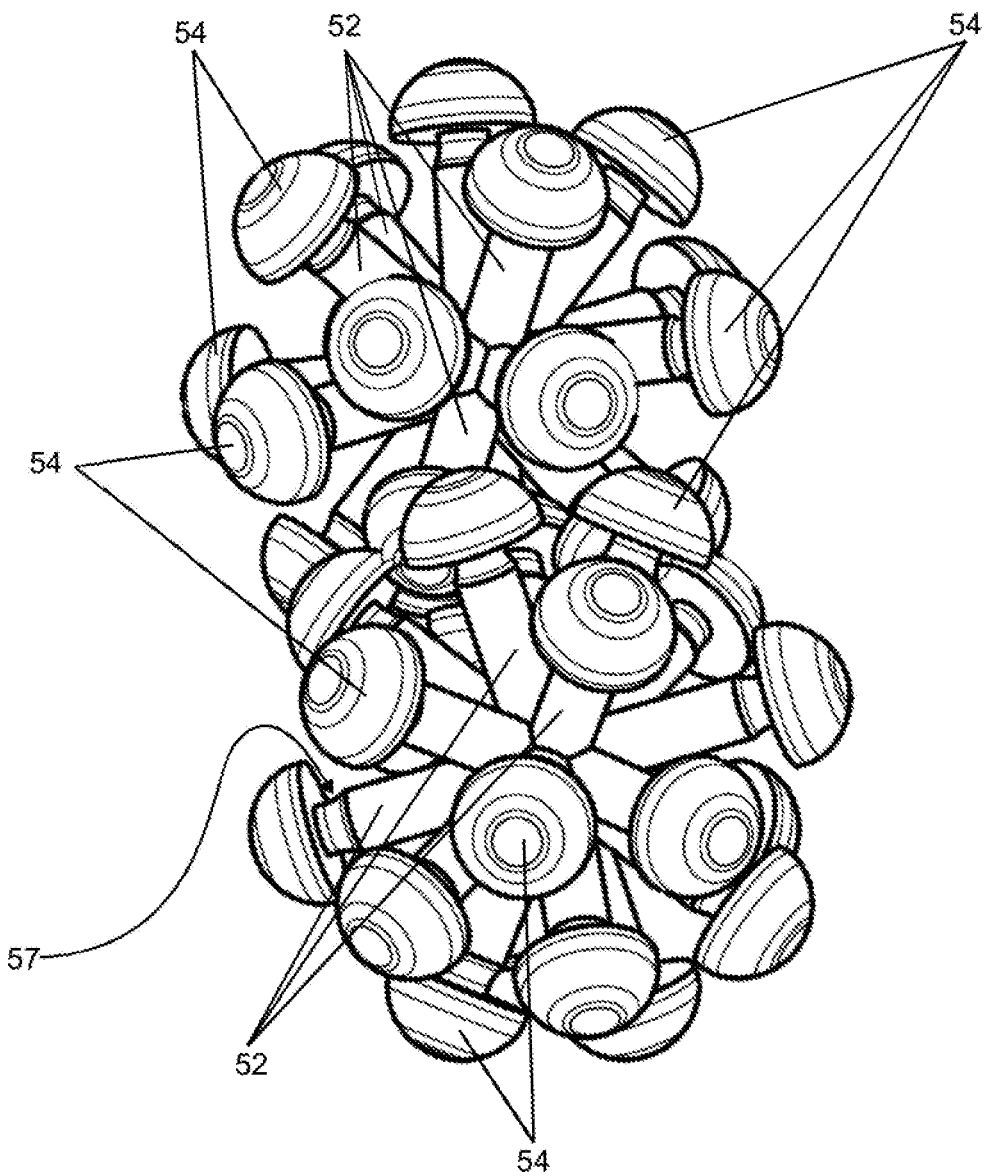
FIG. 13: shows a schematic perspective view of two particles of a fifth alternative bone replacement material according to the invention that are connected to each other.
Figure 14:
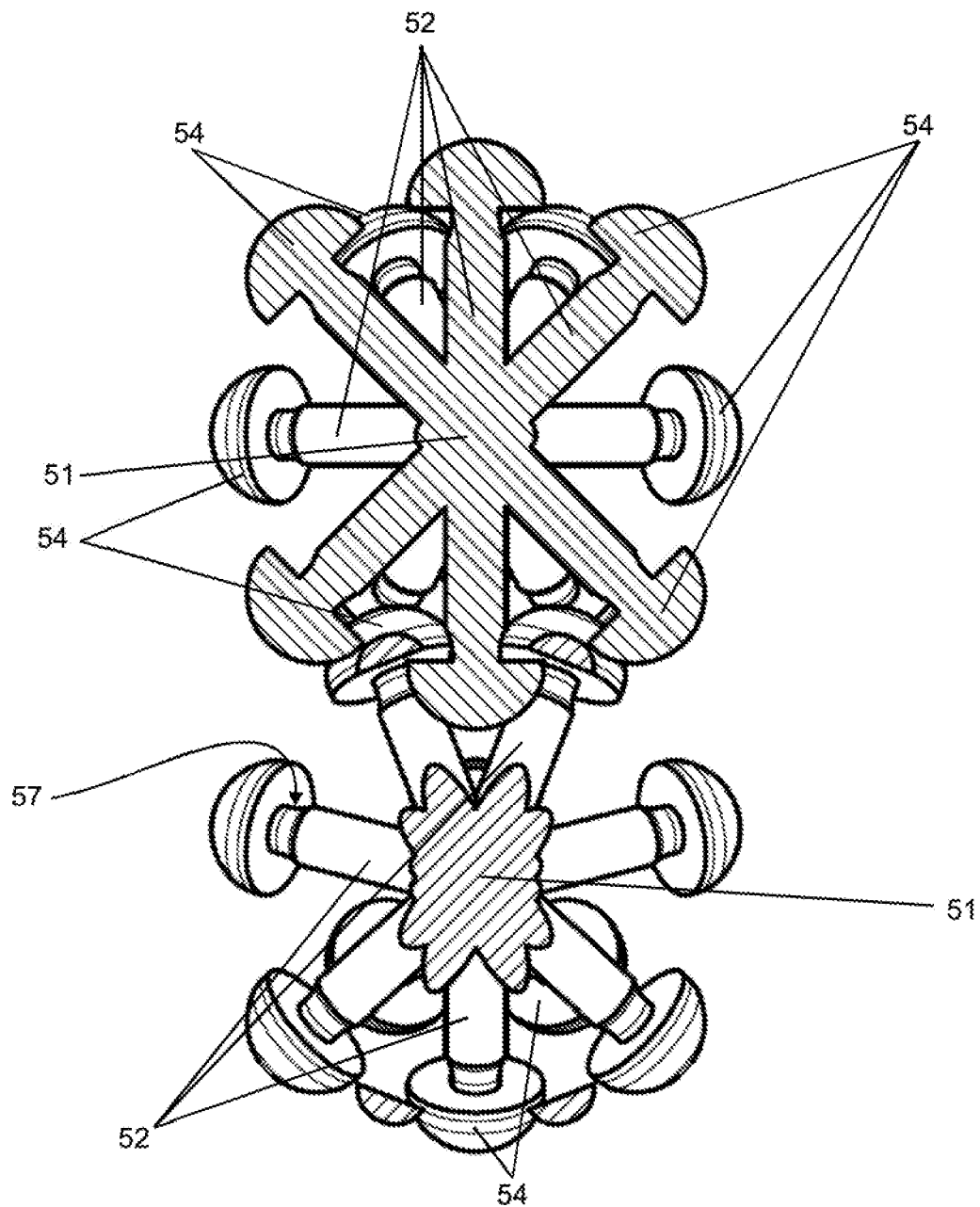
FIG. 14: shows a schematic cross-sectional view of the connected particle according to FIG. 13.

FIG. 13 shows a schematic perspective view of two particles of a fifth alternative alternative bone replacement material according to the invention. FIG. 14 shows a schematic cross-sectional view of the particles of the fifth bone replacement material according to the invention according to FIG. 13 that are connected to each other. The particles consist of tantalum or a tantalum alloy or another biocompatible metal or another biocompatible metal alloy, but can just as well be fabricated from a biocompatible plastic material. The particles are produced through a CAM procedure and/or a 3D printing procedure. All suitable rapid prototyping methods can also be used for producing the particles.

The particles are composed of a core 51 that is arranged in the geometrical centre of the particle as well as twenty pins 52 that extend radially away from the core 51 in various directions. The particle has icosahedral symmetry such that the ends of the pins 52 are arranged on a spherical surface about the centre of the core 51. The ends of the pins 52 have mushrooms 54 connected to the pins 52 as connecting elements. The pins 52 comprise, below the mushrooms 54, a circumferential groove 57 as additional connecting means 57. The pins 52 are cylindrical except for the mushrooms 54 and the groove 57. The mushrooms 54 are spherically rounded towards the outside (away from the core 51). Other types of rounding, such as, for example, ellipsoidal segments, are feasible just as well. The groove 57 of the pins 54 is well-suited for snap-in connection to other mushrooms 54 of engaging particles. Accordingly, the mushrooms 54 form snap-in means 54 and the grooves 57 form opposite snap-in means 57 that snap into each other when the particles are being pressed into each other.

In order to form a bone replacement material according to the invention, the particles preferably are situated to touch against each other, without being connected, such that the mushrooms 54 and grooves 57 of the pins 52 do not engage each other yet. Moreover, the particles can be present in the form of a slurry, in which they are mixed with a liquid. The liquid preferably contains at least one pharmaceutically active substance suitable for controlling an infection or for stimulating bone growth. Alternatively or in addition, the particles can be coated with a pharmaceutically active substance of this type.

The bone replacement material can be formed by pushing the particles into each other. As a result, the particles snap into each other as is shown in FIGS. 13 and 14 and can be seen well in the schematic cross-sectional view according to FIG. 14. In this context, the edges of the mushrooms 54 engage the grooves 57 of the pins 52. In order to get into this position, the pins 52 must be bent elastically towards the side by applying a mechanical pressure onto the particles to be connected. Upon elastic restoration of the pins 52, the mushrooms 54 are pushed into the grooves 57 of the neighbouring mushrooms 54. In the embodiment according to FIGS. 13 and 14, the lengths and diameters of the pins 52 as well as the shape of the grooves 57 and mushrooms 54 are appropriately matched to each other such that the outer curvature of the mushrooms 54 fits perfectly into the grooves 57 of the pins 52. As a result, the mushrooms 54 snap into the grooves 57, since the mushrooms 54 cannot be pushed more deeply into each other without applying a force (i.e. without further elastic deformation of the pins 52). This is no longer possible after multiple snap-in connection of the particles by multiple mushrooms 54 and grooves 57 of one particle and/or multiple particles to another particle. The bone replacement material is thus becoming reinforced as desired. This type of connection of the particles can be applied similarly to the other embodiments according to FIGS. 1 to 11.

In this context, the particles become appropriately connected to each other such that free gaps remain between the particles that are connected to each other such that the three-dimensional body, which is formed from the particles and becomes reinforced, is open-pored. The particles have a diameter of approximately 5 mm such that the remaining pores have a free cross-section in the range of approximately 0.5 mm. Said cross-section is still sufficient to allow bone material to be formed in and/or to grow into the pores. The body with its open pores can therefore be called osteoconductive. To promote the osteoconductivity, the surface of the particles can be coated with a bone growth-promoting substance. The three-dimensional body formed from the particles is therefore well-suited as bone replacement material.

The particles should be pushed firmly into each other such that the three-dimensional body is dimensionally stable. In this context, the particles snap into each other by the mushrooms 54 sliding between the mushrooms 54 of connected particles and thus deforming the pins 52 of connected particles elastically. Due to the elastic restoring force of the pins 52, the mushrooms 54 can be pulled into the grooves 57 of other pins 52 of neighbouring particles. It is feasible just as well that edges of the mushrooms 54 plastically deform the pins 52 of neighbouring particles to a small extent and that the particles are thus snapped into each other.

The features of the invention disclosed in the preceding description and in the claims, figures, and exemplary embodiments, can be essential for the implementation of the various embodiments of the invention both alone and in any combination.

| List of reference numbers | |
|---|---|
| 1, 11, 21, 31, 51 | Core |
| 2, 12, 22, 32, 52 | Pin |
| 4, 14, 34 | Mushroom/connecting element |
| 6, 16 | Gripping surface |
| 25, 35 | Hook/connecting element |
| 37 | Undercut |
| 41 | Planar structure |
| 42 | Pin |
| 44 | Mushroom/connecting element |
| 45 | Hook/connecting element |
| 47 | Groove |
| 54 | Mushroom/connecting element/snap-in means |
| 57 | Groove/opposite snap-in means |

The invention claimed is:

1. Particulate alloplastic bone replacement material comprising a plurality of individual particles not connected to each other, wherein each individual particle of the plurality of individual particles comprises a core and at least six pins extending from the core, wherein the at least six pins of each individual particle comprise at least one connecting element, and wherein, when multiple individual particles of the plurality of individual particles not connected to each other are pressed together, pins of the multiple individual particles elastically deform such that the connecting elements of the different individual particles interlock with and/or snap into each other and the different individual particles that are interlocked with and/or snapped into each other form an open-pored body comprising the different individual particles interlocked with each other and/or snapped into each other, wherein, when the different individual particles are interlocked with each other, neighbouring particles of the different individual particles comprise pins that are readily inseparable from each other and mobile with respect to each other by pressing the neighbouring particles further together, and further wherein, when the different individual particles are snapped into each other, neighbouring particles of the different individual particles comprise pins that engage each other such that the neighbouring particles are readily inseparable from each other and unmovable towards each other by further moving the neighbouring particles without deformation of the neighbouring particles.

2. The bone replacement material according to claim 1, wherein the connecting elements are mushrooms, hooks, undercuts, snap-in elements and/or opposite snap-in means.

3. The bone replacement material according to claim 1, wherein the individual particles are spherical.

4. The bone replacement material according to claim 1, wherein the pins of the individual particles extend radially away from the core.

5. The bone replacement material according to claim 1, wherein additional connecting elements are disposed between the connecting elements and the pins.

6. The bone replacement material according to claim 1, wherein the individual particles that are pressed into each other interlock with and/or snap into each other.

7. The bone replacement material according to claim 1, wherein the individual particles have a maximum cross-section of no more than 10 mm.

8. The bone replacement material according to claim 1, wherein the individual particles are produced with a generative 3D printing procedure.

9. The bone replacement material according to claim 1, wherein at least one of the at least one connecting elements per pin has a truncated cone shape, wherein longitudinal axes of the pins form longitudinal axes of the cones and wherein a jacket of the cones faces toward an outer side that faces away from the core.

10. The bone replacement material according to claim 1, wherein at least one of the at least one connecting elements per pin is provided in the form of a hook or as a mushroom head.

11. The bone replacement material according to claim 1, wherein the pins contain a circumferential groove as an additional connecting element between the core and at least one of the at least one connecting elements, wherein connecting elements of other individual particles can interlock with or snap into said circumferential groove such that no further motion of the connecting elements along the pins is possible.

12. The bone replacement material according to claim 1, wherein at least two connecting elements are arranged in succession on a jacket surface of the pins.

13. The bone replacement material according to claim 1, wherein each individual particle has an icosahedral symmetry and ends of the pins of each individual particle are arranged on a spherical surface about a center of the core of each individual particle.

14. The bone replacement material according to claim 1, wherein the individual particles have a maximum cross-section of more than 1 mm.

15. The bone replacement material according to claim 1, wherein the individual particles are made from materials comprising biocompatible plastic material, stainless steel, titanium, a titanium alloy, tantalum, a tantalum alloy, or composites of the materials.

16. The bone replacement material according to claim 1, wherein neighbouring pins of a first individual particle of the plurality of individual particles are situated at a distance from each other such that the neighbouring pins of the first individual particle, after elastic deformation due to interlocking and/or snapping into a connecting element of a second individual particle of the plurality of individual particles, enable at least two interlocks and/or snap-in connections to the first and second individual particles.

17. The bone replacement material according to claim 1, wherein the individual particles are suspended in an aqueous or non-aqueous solution of biocompatible polymers and/or oligomers, and the individual particles and the solution, together, form a pasty mass.

18. The bone replacement material according to claim 1, wherein the individual particles are suspended in a low-molecular liquid that is hydrophobic at room temperature, and the individual particles and the liquid, together, form a pasty mass.

19. The bone replacement material according to claim 1, wherein the individual particles are mixed with inorganic or organic particulate bone replacement material and/or autologous or, also, allogenic cancellous bone.

20. The bone replacement material according to claim 1, wherein the individual particles are suspended in a biocompatible liquid that contains one or more pharmaceutical agents, whereby the pharmaceutical agent or agents is/are suspended and/or dissolved in the liquid.

21. The bone replacement material according to claim 1, wherein the individual particles are coated with one or more pharmaceutical agents from the groups of antibiotics, bisphosphonates, steroids, non-steroidal anti-inflammatory drugs, growth factors, and cytostatic agents.

22. The bone replacement material according to claim 1, wherein the individual particles comprise at least fourteen pins extending from the core.

23. Implant material configured for trauma surgery, orthopaedics, or veterinary medicine, the implant material comprising the bone replacement material according to claim 1, wherein a porous body of the bone replacement material is formed through interlinking of the individual particles of the bone replacement material by compression of the individual particles that touch against each other.

* * * * *